(12) United States Patent
Mitchell

(10) Patent No.: US 7,273,496 B2
(45) Date of Patent: Sep. 25, 2007

(54) ARTIFICIAL VERTEBRAL DISK REPLACEMENT IMPLANT WITH CROSSBAR SPACER AND METHOD

(75) Inventor: Steve Mitchell, Pleasant Hill, CA (US)

(73) Assignee: St. Francis Medical Technologies, Inc., Concord, CA (US)

( * ) Notice: Subject to any disclaimer, the term of this patent is extended or adjusted under 35 U.S.C. 154(b) by 0 days.

(21) Appl. No.: 10/684,668

(22) Filed: Oct. 14, 2003

(65) Prior Publication Data

US 2004/0172135 A1    Sep. 2, 2004

Related U.S. Application Data

(60) Provisional application No. 60/422,021, filed on Oct. 29, 2002.

(51) Int. Cl.
 *A61F 2/44* (2006.01)
(52) U.S. Cl. .................... 623/17.14; 623/17.15
(58) Field of Classification Search ........... 623/17.11, 623/17.14, 17.15, 17.16, 48
See application file for complete search history.

(56) References Cited

U.S. PATENT DOCUMENTS

| | | | |
|---|---|---|---|
| 2,456,806 A | 12/1948 | Wolffe | |
| 2,677,369 A | 5/1954 | Knowles | ........................ 128/92 |
| 3,648,691 A | 3/1972 | Lumb | ........................ 128/92 |
| 3,867,728 A | 2/1975 | Stubstad et al. | |
| 3,875,595 A | 4/1975 | Froning | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,479,491 A | 10/1984 | Martin | |
| 4,499,613 A * | 2/1985 | Yarrow | ........................ 623/48 |
| 4,501,269 A | 2/1985 | Bagby | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,636,217 A | 1/1987 | Ogilvie | |

(Continued)

FOREIGN PATENT DOCUMENTS

CA    2015507    1/1991

(Continued)

OTHER PUBLICATIONS

Ceramic Interspinous Block (CISB) Assisted Anterior Interbody Fusion, Haruo Tsuji, Norikazu Hirano, Yoshiharu Katoh, Hiroshi Ohsima, Hirokazu Ishihara, Hisao Matsui, and Yohihiko Hayashi, *Journal of Spinal Disorders* vol. 3. No. 1, pp. 77-86, c1990 Raven Press, Ltd., New York.

(Continued)

*Primary Examiner*—Bruce Snow
(74) *Attorney, Agent, or Firm*—Townsend and Townsend and Crew LLP

(57) ABSTRACT

The present invention is directed to a device with that can be placed between two vertebrae. The implant is characterized by having a first plate and a second plates with a crossbar therebetween. The crossbar fits within cavities on each of the first and second plate and allows for pivotal or rotational motion and also for twisting motion.

19 Claims, 8 Drawing Sheets

U.S. PATENT DOCUMENTS

| | | |
|---|---|---|
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Buttner-Janz et al. |
| 4,759,769 A | 7/1988 | Hedman et al. |
| 4,772,287 A | 9/1988 | Ray et al. |
| 4,790,303 A | 12/1988 | Steffee |
| 4,834,757 A | 5/1989 | Brantigan |
| 4,863,477 A | 9/1989 | Monson |
| 4,874,389 A | 10/1989 | Downey |
| 4,904,260 A | 2/1990 | Ray et al. |
| 4,904,261 A | 2/1990 | Dove et al. |
| 4,911,718 A | 3/1990 | Lee et al. |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 4,997,432 A | 3/1991 | Keller |
| 5,002,576 A | 3/1991 | Furhmann et al. |
| 5,011,484 A | 4/1991 | Breard ............... 606/61 |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,071,437 A | 12/1991 | Steffee |
| 5,108,438 A | 4/1992 | Stone |
| 5,108,442 A | 4/1992 | Smith |
| 5,122,130 A | 6/1992 | Keller |
| 5,123,926 A | 6/1992 | Pisharodi |
| 5,167,662 A | 12/1992 | Hayes et al. |
| 5,171,280 A | 12/1992 | Baumgartner |
| 5,171,281 A | 12/1992 | Parsons et al. |
| 5,180,381 A | 1/1993 | Aust et al. |
| 5,192,326 A | 3/1993 | Bao et al. |
| 5,192,327 A | 3/1993 | Brantigan |
| 5,246,458 A | 9/1993 | Graham |
| 5,258,031 A | 11/1993 | Salib et al. |
| 5,258,043 A | 11/1993 | Stone |
| 5,263,953 A | 11/1993 | Bagby |
| 5,290,312 A | 3/1994 | Kojimoto et al. |
| 5,306,307 A | 4/1994 | Senter |
| 5,306,308 A | 4/1994 | Gross et al. |
| 5,306,309 A | 4/1994 | Wagner et al. |
| 5,313,962 A | 5/1994 | Obenchain |
| 5,314,477 A | 5/1994 | Marnay |
| 5,314,478 A | 5/1994 | Oka et al. |
| 5,320,644 A | 6/1994 | Baumgartner |
| 5,336,223 A | 8/1994 | Rogers |
| 5,350,397 A | 9/1994 | Palermo et al. |
| 5,352,225 A | 10/1994 | Yuan et al. |
| 5,354,302 A | 10/1994 | Ko |
| 5,360,430 A | 11/1994 | Lin |
| 5,366,508 A | 11/1994 | Brekke |
| 5,370,693 A | 12/1994 | Kelman et al. |
| 5,370,697 A | 12/1994 | Baumgartner |
| 5,375,823 A | 12/1994 | Navas |
| 5,383,884 A | 1/1995 | Summers |
| 5,395,317 A | 3/1995 | Kambin |
| 5,395,372 A | 3/1995 | Holt et al. |
| 5,397,364 A | 3/1995 | Kozak et al. |
| 5,401,269 A | 3/1995 | Buttner-Janz et al. |
| 5,415,704 A | 5/1995 | Davidson |
| 5,423,816 A | 6/1995 | Lin |
| 5,423,817 A | 6/1995 | Lin |
| 5,425,772 A | 6/1995 | Brantigan |
| 5,425,773 A | 6/1995 | Boyd et al. |
| 5,425,777 A | 6/1995 | Sarkisian et al. |
| 5,431,658 A | 7/1995 | Moskovich |
| 5,439,464 A | 8/1995 | Shapiro |
| 5,443,514 A | 8/1995 | Steffee |
| 5,443,515 A | 8/1995 | Cohen et al. |
| 5,445,639 A | 8/1995 | Kuslich et al. |
| 5,454,812 A | 10/1995 | Lin |
| 5,456,722 A | 10/1995 | McLeod et al. |
| 5,458,638 A | 10/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,480,401 A | 1/1996 | Navas |
| 5,480,442 A | 1/1996 | Bertagnoli |
| 5,484,437 A | 1/1996 | Michelson |
| 5,489,307 A | 2/1996 | Kuslich et al. |
| 5,489,308 A | 2/1996 | Kuslich et al. |
| 5,496,318 A | 3/1996 | Howland ............... 606/61 |
| 5,505,732 A | 4/1996 | Michelson |
| 5,507,816 A | 4/1996 | Bullivant |
| 5,514,180 A | 5/1996 | Heggeness et al. |
| 5,522,899 A | 6/1996 | Michelson |
| 5,527,312 A | 6/1996 | Ray |
| 5,531,793 A | 7/1996 | Kelman et al. |
| 5,534,023 A | 7/1996 | Henley |
| 5,534,028 A | 7/1996 | Bao et al. |
| 5,534,029 A | 7/1996 | Shima |
| 5,534,030 A | 7/1996 | Navarro et al. |
| 5,534,031 A | 7/1996 | Matsuzaki et al. |
| 5,540,689 A | 7/1996 | Sanders et al. |
| 5,545,229 A | 8/1996 | Parsons et al. |
| 5,549,679 A | 8/1996 | Kuslich |
| 5,554,191 A | 9/1996 | Lahille et al. |
| 5,556,431 A | 9/1996 | Buttner-Janz |
| 5,562,736 A | 10/1996 | Ray et al. |
| 5,562,738 A | 10/1996 | Boyd et al. |
| 5,571,109 A | 11/1996 | Bertagnoli |
| 5,571,189 A | 11/1996 | Kuslich |
| 5,571,190 A | 11/1996 | Ulrich et al. |
| 5,571,192 A | 11/1996 | Schönhöffer |
| 5,591,235 A | 1/1997 | Kuslich |
| 5,593,409 A | 1/1997 | Michelson |
| 5,599,279 A | 2/1997 | Slotman et al. |
| 5,601,556 A | 2/1997 | Pisharodi |
| 5,609,634 A | 3/1997 | Voydeville ............... 623/17 |
| 5,609,635 A | 3/1997 | Michelson |
| 5,609,636 A | 3/1997 | Kohrs et al. |
| 5,620,458 A | 4/1997 | Green et al. |
| 5,645,592 A | 7/1997 | Nicolais et al. |
| 5,645,596 A | 7/1997 | Kim et al. |
| 5,645,597 A | 7/1997 | Krapiva |
| 5,645,598 A | 7/1997 | Brosnahan, III |
| 5,645,599 A | 7/1997 | Samani |
| 5,653,761 A | 8/1997 | Pisharodi |
| 5,653,762 A | 8/1997 | Pisharodi |
| 5,658,335 A | 8/1997 | Allen |
| 5,658,336 A | 8/1997 | Pisharodi |
| 5,658,337 A | 8/1997 | Kohrs et al. |
| 5,669,909 A | 9/1997 | Zdeblick et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,463 A | 11/1997 | Godefroy et al. |
| 5,683,464 A | 11/1997 | Wagner et al. |
| 5,683,465 A | 11/1997 | Shinn et al. |
| 5,693,100 A | 12/1997 | Pisharodi |
| 5,697,889 A | 12/1997 | Slotman et al. |
| 5,697,977 A | 12/1997 | Pisharodi |
| 5,700,292 A | 12/1997 | Margulies |

| | | | | | |
|---|---|---|---|---|---|
| 5,702,449 A | 12/1997 | McKay | 6,096,038 A | 8/2000 | Michelson |
| 5,702,450 A | 12/1997 | Bisserie | 6,096,080 A | 8/2000 | Nicholson et al. |
| 5,702,454 A | 12/1997 | Baumgartner | 6,099,531 A | 8/2000 | Bonutti |
| 5,702,455 A | 12/1997 | Saggar | 6,102,950 A | 8/2000 | Vaccaro |
| 5,716,415 A | 2/1998 | Steffee | 6,110,210 A | 8/2000 | Norton et al. |
| 5,716,416 A | 2/1998 | Lin | 6,111,164 A | 8/2000 | Rainey et al. |
| 5,741,253 A | 4/1998 | Michelson | 6,113,637 A | 9/2000 | Gill et al. |
| 5,755,732 A | 5/1998 | Green et al. | 6,113,638 A | 9/2000 | Williams et al. |
| 5,755,796 A | 5/1998 | Ibo et al. | 6,113,639 A | 9/2000 | Ray et al. |
| 5,755,798 A | 5/1998 | Papavero et al. | 6,120,502 A | 9/2000 | Michelson |
| 5,766,252 A | 6/1998 | Henry et al. | 6,120,503 A | 9/2000 | Michelson |
| 5,772,661 A | 6/1998 | Michelson | 6,123,705 A | 9/2000 | Michelson |
| 5,776,196 A | 7/1998 | Matsuzaki et al. | 6,126,689 A | 10/2000 | Brett |
| 5,776,199 A | 7/1998 | Michelson | 6,127,597 A | 10/2000 | Beyar et al. |
| 5,782,830 A | 7/1998 | Farris | 6,129,763 A | 10/2000 | Chauvin et al. |
| 5,782,832 A | 7/1998 | Larsen et al. | 6,132,430 A | 10/2000 | Wagner |
| 5,782,919 A | 7/1998 | Zdeblick et al. | 6,132,465 A | 10/2000 | Ray et al. |
| 5,797,909 A | 8/1998 | Michelson | 6,136,001 A | 10/2000 | Michelson |
| 5,800,438 A | 9/1998 | Tuke et al. | 6,136,031 A | 10/2000 | Middleton |
| 5,800,550 A | 9/1998 | Sertich | 6,139,579 A | 10/2000 | Steffee et al. |
| 5,824,093 A | 10/1998 | Ray et al. | 6,146,421 A | 11/2000 | Gordon et al. |
| 5,824,094 A | 10/1998 | Serhan et al. | 6,146,422 A | 11/2000 | Lawson |
| 5,827,328 A | 10/1998 | Buttermann | 6,149,650 A | 11/2000 | Michelson |
| 5,836,948 A | 11/1998 | Zucherman et al. | 6,149,652 A | 11/2000 | Zucherman et al. |
| 5,860,973 A | 1/1999 | Michelson | 6,149,686 A | 11/2000 | Kuslich et al. |
| 5,860,977 A | 1/1999 | Zucherman et al. | 6,152,926 A | 11/2000 | Zucherman et al. |
| 5,865,845 A | 2/1999 | Thalgott | 6,156,038 A | 12/2000 | Zucherman et al. |
| 5,865,846 A | 2/1999 | Bryan et al. | 6,156,067 A | 12/2000 | Bryan et al. |
| 5,876,404 A | 3/1999 | Zucherman et al. | 6,159,215 A | 12/2000 | Urbahns et al. |
| 5,885,292 A | 3/1999 | Moskovitz et al. | 6,162,252 A | 12/2000 | Kuras et al. |
| 5,885,299 A | 3/1999 | Winslow et al. | 6,165,218 A | 12/2000 | Husson et al. |
| 5,888,222 A | 3/1999 | Coates et al. | 6,176,882 B1 | 1/2001 | Biedermann et al. |
| 5,888,224 A | 3/1999 | Beckers et al. | 6,179,874 B1 | 1/2001 | Cauthen |
| 5,888,226 A | 3/1999 | Rogozinski | 6,183,471 B1 | 2/2001 | Zucherman et al. |
| 5,891,147 A | 4/1999 | Moskovitz et al. | 6,190,387 B1 | 2/2001 | Zucherman et al. |
| 5,893,889 A | 4/1999 | Harrington | 6,190,414 B1 | 2/2001 | Young et al. |
| 5,893,890 A | 4/1999 | Pisharodi | 6,193,757 B1 | 2/2001 | Foley et al. |
| 5,895,426 A | 4/1999 | Scarborough et al. | 6,206,922 B1 | 3/2001 | Zdeblick et al. |
| 5,895,427 A | 4/1999 | Kuslich et al. | 6,210,412 B1 | 4/2001 | Michelson |
| 5,895,428 A | 4/1999 | Berry | 6,224,595 B1 | 5/2001 | Michelson |
| 5,899,941 A | 5/1999 | Nishijima et al. | 6,224,631 B1 | 5/2001 | Kohrs |
| 5,906,616 A | 5/1999 | Pavlov et al. | 6,228,118 B1 | 5/2001 | Gordon |
| 5,919,235 A | 7/1999 | Husson et al. | 6,231,609 B1 | 5/2001 | Mehdizadeh |
| 5,928,284 A | 7/1999 | Mehdizadeh | 6,234,705 B1 | 5/2001 | Troxell |
| 5,944,754 A | 8/1999 | Vacanti | 6,235,030 B1 | 5/2001 | Zucherman et al. |
| 5,945,115 A | 8/1999 | Dunn et al. | 6,238,397 B1 | 5/2001 | Zucherman et al. |
| 5,961,554 A | 10/1999 | Janson et al. | 6,241,769 B1 | 6/2001 | Nicholson et al. |
| 5,964,807 A | 10/1999 | Gan et al. | 6,241,770 B1 | 6/2001 | Michelson |
| 5,976,186 A | 11/1999 | Bao et al. | 6,241,771 B1 | 6/2001 | Gresser et al. |
| 5,980,572 A | 11/1999 | Kim et al. | 6,245,072 B1 | 6/2001 | Zdeblick et al. |
| 5,984,967 A | 11/1999 | Zdeblick et al. | 6,245,108 B1 | 6/2001 | Biscup |
| 5,989,291 A | 11/1999 | Ralph et al. | 6,261,296 B1 | 7/2001 | Aebi et al. |
| 6,001,130 A | 12/1999 | Bryan et al. | 6,264,655 B1 | 7/2001 | Pisharodi |
| 6,004,573 A | 12/1999 | Rathi et al. | 6,264,656 B1 | 7/2001 | Michelson |
| 6,005,162 A | 12/1999 | Constantz | 6,264,695 B1 | 7/2001 | Stoy |
| 6,019,792 A | 2/2000 | Cauthen | 6,270,498 B1 | 8/2001 | Michelson |
| 6,019,793 A | 2/2000 | Perren et al. | 6,277,149 B1 | 8/2001 | Boyle et al. |
| 6,022,376 A | 2/2000 | Assell et al. | 6,280,444 B1 | 8/2001 | Zucherman et al. |
| 6,039,761 A | 3/2000 | Li et al. | 6,280,475 B1 | 8/2001 | Bao et al. |
| 6,039,763 A | 3/2000 | Shelokov | 6,287,343 B1 | 9/2001 | Kuslich et al. |
| 6,042,582 A | 3/2000 | Ray | 6,296,664 B1 | 10/2001 | Middleton |
| 6,045,579 A | 4/2000 | Hochshuler et al. | 6,296,665 B1 | 10/2001 | Strnad et al. |
| 6,045,580 A | 4/2000 | Scarborough et al. | 6,302,914 B1 | 10/2001 | Michelson |
| 6,048,342 A | 4/2000 | Zucherman | 6,309,421 B1 | 10/2001 | Pisharodi |
| 6,051,648 A | 4/2000 | Rhee et al. | 6,311,562 B1 | 11/2001 | Hanada |
| 6,068,630 A | 5/2000 | Zucherman | 6,315,795 B1 | 11/2001 | Scarborough et al. |
| 6,074,390 A | 6/2000 | Zucherman et al. | 6,315,797 B1 | 11/2001 | Middleton |
| 6,080,155 A | 6/2000 | Michelson | 6,325,827 B1 | 12/2001 | Lin |
| 6,080,158 A | 6/2000 | Lin | 6,332,882 B1 | 12/2001 | Zucherman et al. |
| 6,080,193 A | 6/2000 | Hochshuler et al. | 6,332,883 B1 | 12/2001 | Zucherman et al. |
| 6,086,613 A | 7/2000 | Camino et al. | 6,342,074 B1 | 1/2002 | Simpson |
| 6,090,112 A | 7/2000 | Zucherman et al. | 6,348,071 B1 | 2/2002 | Steffee et al. |
| 6,093,205 A | 7/2000 | McLeod et al. | 6,350,283 B1 | 2/2002 | Michelson |

| | | |
|---|---|---|
| 6,364,880 B1 | 4/2002 | Michelson |
| 6,368,350 B1 | 4/2002 | Erickson et al. |
| 6,368,351 B1 | 4/2002 | Glenn et al. |
| 6,371,984 B1 | 4/2002 | Van Dyke et al. |
| 6,371,988 B1 | 4/2002 | Pafford et al. |
| 6,371,989 B1 | 4/2002 | Chauvin et al. |
| 6,379,355 B1 | 4/2002 | Zucherman et al. |
| 6,379,385 B1 | 4/2002 | Kalas et al. |
| 6,383,221 B1 | 5/2002 | Scarborough et al. |
| 6,391,030 B1 | 5/2002 | Wagner et al. |
| 6,391,058 B1 | 5/2002 | Kuslich et al. |
| 6,395,030 B1 | 5/2002 | Songer et al. |
| 6,395,031 B1 | 5/2002 | Foley et al. |
| 6,395,032 B1 | 5/2002 | Gauchet |
| 6,395,034 B1 | 5/2002 | Suddaby |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoech et al. |
| 6,425,920 B1 | 7/2002 | Hamada |
| 6,432,106 B1 | 8/2002 | Fraser |
| 6,436,098 B1 | 8/2002 | Michelson |
| 6,436,119 B1 | 8/2002 | Erb et al. |
| 6,436,140 B1 | 8/2002 | Liu et al. |
| 6,436,142 B1 | 8/2002 | Paes et al. |
| 6,440,168 B1 | 8/2002 | Cauthen |
| 6,440,169 B1 | 8/2002 | Elberg et al. |
| 6,443,990 B1 | 9/2002 | Aebi et al. |
| 6,447,512 B1 | 9/2002 | Landry et al. |
| 6,447,544 B1 | 9/2002 | Michelson |
| 6,447,547 B1 | 9/2002 | Michelson |
| 6,451,019 B1 | 9/2002 | Zucherman et al. |
| 6,451,020 B1 | 9/2002 | Zucherman et al. |
| 6,454,804 B1 | 9/2002 | Ferree |
| 6,454,807 B1 | 9/2002 | Jackson |
| 6,458,131 B1 | 10/2002 | Ray |
| 6,458,159 B1 | 10/2002 | Thalgott |
| 6,461,359 B1 | 10/2002 | Tribus et al. |
| 6,468,310 B1 | 10/2002 | Ralph et al. |
| 6,471,724 B2 | 10/2002 | Zdeblick et al. |
| 6,475,219 B1 | 11/2002 | Shelokov |
| 6,478,796 B2 | 11/2002 | Zucherman et al. |
| 6,478,822 B1 | 11/2002 | Leroux et al. |
| 6,478,823 B1 | 11/2002 | Michelson |
| 6,482,233 B1 | 11/2002 | Aebi et al. |
| 6,482,235 B1 | 11/2002 | Lambrecht et al. |
| 6,485,517 B1 | 11/2002 | Michelson |
| 6,488,710 B2 | 12/2002 | Besselink |
| 6,500,178 B2 | 12/2002 | Zucherman et al. |
| 6,500,205 B1 | 12/2002 | Michelson |
| 6,503,279 B1 | 1/2003 | Webb et al. |
| 6,514,256 B2 | 2/2003 | Zucherman et al. |
| 6,517,580 B1 | 2/2003 | Ramadan et al. |
| 6,520,993 B2 | 2/2003 | James et al. |
| 6,520,996 B1 | 2/2003 | Manasas et al. |
| 6,524,312 B2 | 2/2003 | Landry et al. |
| 6,527,773 B1 | 3/2003 | Lin et al. |
| 6,527,804 B1 | 3/2003 | Gauchet et al. |
| 6,527,806 B2 | 3/2003 | Ralph et al. |
| 6,530,933 B1 | 3/2003 | Yeung et al. |
| 6,530,955 B2 | 3/2003 | Boyle et al. |
| 6,540,785 B1 | 4/2003 | Gill et al. |
| 6,547,823 B2 | 4/2003 | Scarborough et al. |
| 6,548,002 B2 | 4/2003 | Gresser et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,073 B2 | 5/2003 | Foley |
| 6,562,074 B2 | 5/2003 | Gerbec et al. |
| 6,565,570 B2 | 5/2003 | Sterett et al. |
| 6,569,201 B2 | 5/2003 | Moumene et al. |
| 6,572,653 B1 | 6/2003 | Simonson |
| 6,572,654 B1 | 6/2003 | Santilli |
| 6,575,982 B1 | 6/2003 | Bonutti |
| 6,576,016 B1 | 6/2003 | Hochshuler et al. |
| 6,576,017 B2 | 6/2003 | Foley et al. |
| 6,579,318 B2 | 6/2003 | Varga et al. |
| 6,579,320 B1 | 6/2003 | Gauchet et al. |
| 6,579,321 B1 | 6/2003 | Gordon et al. |
| 6,582,432 B1 | 6/2003 | Michelson |
| 6,582,437 B2 | 6/2003 | Dorchak et al. |
| 6,582,468 B1 | 6/2003 | Gauchet |
| 6,626,944 B1 | 9/2003 | Taylor |
| 6,682,562 B2 | 1/2004 | Viart et al. |
| 6,699,246 B2 | 3/2004 | Zucherman et al. |
| 6,706,068 B2 | 3/2004 | Ferree |
| 6,706,070 B1 * | 3/2004 | Wagner et al. ............ 623/17.15 |
| 6,740,118 B2 | 5/2004 | Eisermann et al. |
| 6,755,841 B2 | 6/2004 | Fraser et al. |
| 6,770,095 B2 | 8/2004 | Grinberg et al. .......... 623/17.14 |
| 2001/0012938 A1 | 8/2001 | Zucherman et al. |
| 2002/0128715 A1 | 9/2002 | Bryan et al. |
| 2003/0204261 A1 * | 10/2003 | Eisermann et al. ....... 623/17.14 |
| 2003/0208273 A1 | 11/2003 | Eisermann et al. |
| 2004/0073313 A1 | 4/2004 | Link et al. |
| 2004/0106998 A1 * | 6/2004 | Ferree ....................... 623/17.16 |
| 2004/0117022 A1 | 6/2004 | Marnay et al. |
| 2004/0138750 A1 | 7/2004 | Mitchell |
| 2004/0143332 A1 | 7/2004 | Krueger et al. |
| 2004/0153157 A1 * | 8/2004 | Keller ....................... 623/17.14 |
| 2004/0225360 A1 | 11/2004 | Malone |
| 2004/0225365 A1 | 11/2004 | Eisermann et al. |
| 2004/0225366 A1 | 11/2004 | Eisermann et al. |
| 2004/0243240 A1 * | 12/2004 | Beaurain et al. .......... 623/17.14 |
| 2006/0036326 A1 * | 2/2006 | Baumgartner et al. ... 623/17.15 |

FOREIGN PATENT DOCUMENTS

| | | |
|---|---|---|
| DE | 3113142 | 1/1982 |
| DE | 4012622 | 7/1991 |
| EP | 0307241 B1 | 3/1989 |
| EP | 0322334 | 6/1989 |
| FR | 2722980 | 7/1994 |
| FR | 2705227 | 11/1994 |
| FR | 2707864 | 1/1995 |
| FR | 2717066 | 9/1995 |
| FR | 2717068 | 9/1995 |
| FR | 2722088 | 1/1996 |
| FR | 2724554 | 3/1996 |
| FR | 2730156 A1 | 8/1996 |
| FR | 2780269 A1 | 12/1999 |
| FR | 2806614 A1 | 9/2001 |
| GB | 780652 | 8/1957 |
| WO | WO90/00037 | 1/1990 |
| WO | WO95/31158 A | 11/1995 |
| WO | WO99/26562 | 6/1999 |
| WO | WO99/59669 | 11/1999 |
| WO | WO 00/04851 | 2/2000 |
| WO | WO 00/13619 | 3/2000 |
| WO | WO 00/13620 | 3/2000 |
| WO | 01/01893 A1 | 1/2001 |

OTHER PUBLICATIONS

Instrumentation and Implants for Spinal Surgery , J. Dabb, *Diary of the XVIIIth Scientific Meeting of the PTO Tr/Pamietnik XVIII Zjazdu Naukowego PTO Tr/PA,WL, Warszawa*, Link America Inc., 1971, 665.

Spinal Stenosis and Neurogenic Claudication, Richard W. Porter, MD, FRCS, FRCSE, *SPINE* vol. 21, No. 17, pp. 2046-2052, c1996, Lippincott-Raven Publishers.

Preliminary Design and Experimental Studies of a Novel Soft Implant for Correcting Sagittal Plan Instability in the Lumbar Spine, R.J.Minns, BEng, Msc, PhD, DscTech, and W.K. Walsh, FRCS, *SPINE* vol. 22, No. 16, pp. 1819-1827, c1997, Lippincott-Raven Publishers.

International Search Report for PCT/US06/10521 (mailed Nov. 22, 2006).

* cited by examiner

ARTIFICIAL VERTEBRAL DISK REPLACEMENT IMPLANT WITH CROSSBAR SPACER AND METHOD

CLAIM OF PRIORITY

This application claims priority to U.S. Provisional Application No. 60/422,021, filed on Oct. 29, 2002, entitled "ARTIFICIAL VERTEBRAL DISK REPLACEMENT IMPLANT WITH CROSSBAR SPACER AND METHOD", which is included herein by reference.

CROSS-REFERENCE TO RELATED APPLICATIONS

This application is related to U.S. Provisional Application No. 60/422,039, filed Oct. 29, 2002, entitled "ARTIFICIAL VERTEBRAL DISK REPLACEMENT IMPLANT WITH TRANSLATING PIVOT POINT AND METHOD,", U.S. patent application Ser. No. 10/684,669, filed Oct. 14, 2003, entitled "ARTIFICIAL VERTEBRAL DISK REPLACEMENT IMPLANT WITH TRANSLATING PIVOT POINT AND METHOD", U.S. Provisional Application No. 60/422,011, filed Oct. 29,2002, entitled "TOOLS FOR IMPLANTING AN ARTIFICIAL VERTEBRAL DISK AND METHOD", U.S. patent application Ser. No. 10/685,134, filed Oct. 14, 2003, entitled "TOOLS FOR IMPLANTING AN ARTIFICIAL VERTEBRAL DISK AND METHOD", U.S. Provisional Application No. 60/422,022, filed Oct. 29, 2002, entitled "ARTIFICIAL VERTEBRAL DISK REPLACEMENT IMPLANT WITH A SPACER AND METHOD,", and U.S. patent application Ser. No. 10/685,011, filed Oct. 14, 2003, entitled "ARTIFICIAL VERTEBRAL DISK REPLACEMENT IMPLANT WITH SPACER AND METHOD,", which are incorporated herein by reference.

FIELD OF THE INVENTION

This invention relates to an artificial vertebral disk replacement and method.

BACKGROUND OF THE INVENTION

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs, (2) complex physiological motion between these parts, and (3) protection of the spinal cord and nerve roots.

As the present society ages, it is anticipated that there will be an increase in adverse spinal conditions which are characteristic of older people. Pain associated with such conditions can be relieved by medication and/or surgery. Of course, it is desirable to eliminate the need for major surgery for all individuals, and, in particular, for the elderly.

More particularly, over the years, a variety of intervertebral implants have been developed in an effort to relieve the pain associated with degenerative and dysfunctional disk conditions. For example, U.S. Pat. No. 4,349,921 to Kuntz discloses an intervertebral disk prosthesis. The Kuntz prosthesis is designed to restore the space between the disks.

U.S. Pat. No. 4,714,469 to Kenna discloses a spinal implant that fuses vertebrae to the implant. The implant has a rigid body that fits between the vertebra with a protuberance extending from a vertebral contacting surface and extends into the vertebral body.

U.S. Pat. No. 5,258,031 to Salib et al. discloses another prosthetic disk with a ball that fits into a socket.

U.S. Pat. Nos. 5,425,773 and 5,562,738 are related patents to Boyd et al. that disclose a disk arthroplasty device for replacement of the spinal disk. A ball-and-socket are provided to enable rotation.

U.S. Pat. No. 5,534,029 to Shima discloses an articulated vertebral body spacer with a pair of upper and lower joint pieces inserted between the vertebra. An intermediate layer is provided to allow for movement between the upper joint piece and the lower joint piece.

U.S. Pat. No. 5,782,832 to Larsen et al. discloses a two-piece ball-and-socket spinal implant with upper and lower plates for insertion within the intervertebral space.

U.S. Pat. No. 6,156,067 to Bryan et al. discloses a prosthesis having two plates with a nucleus therebetween.

None of these solutions provide an implant that restores a wide range of natural movement.

Accordingly, there needs to be developed implants for alleviating such conditions and restoring natural movement.

SUMMARY OF THE INVENTION

Embodiments of the present invention are directed to providing an implant for alleviating discomfort associated with the spinal column. One embodiment of the implant is characterized by having a first plate and a second plate with a crossbar therebetween.

Other aspects, objects, features and elements of embodiments of the invention are described or are evident from the accompanying specification, claims and figures.

DETAILED DESCRIPTION OF THE PREFERRED EMBODIMENTS OF THE INVENTION

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference.

Figure 1A:
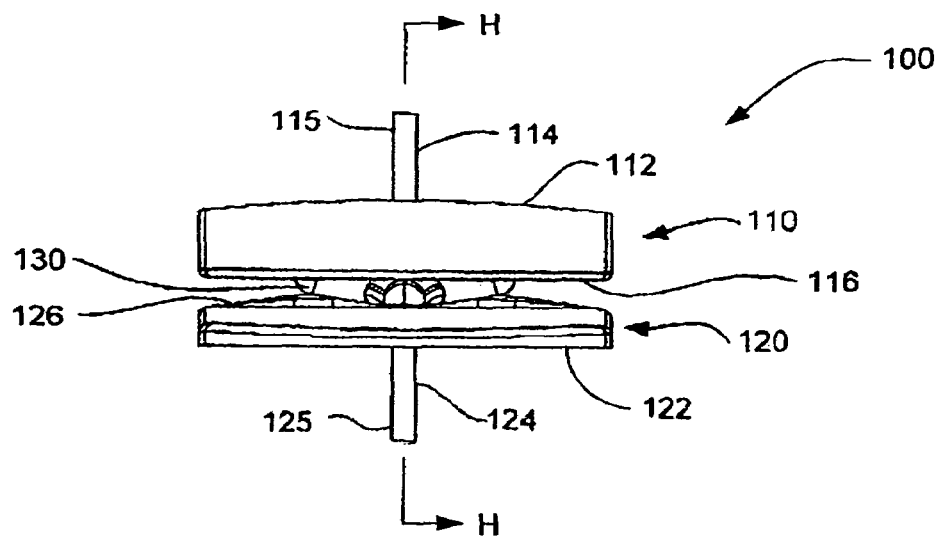
FIG. 1A is a front view of an embodiment of an implant of the invention.

FIG. 1A shows an embodiment of the implant 100 of the invention. The implant 100 has a first part or plate or piece or spacer member 110 that is configured to mate with a first vertebra and a second part or plate or piece or spacer member 120 that is configured to mate with a second vertebra. The first plate or implant 110 is an upper plate and the second plate or implant 120 is a lower plate. A third part 130 that sits between the first plate 110 and the second plate 120 is also provided. The third part 130 acts as a spacer between the first plate 110 and the second plate 120 and facilitates pivotal or rotational and also twisting movement of the first plate 110 and the second plate 120, relative to each other. The third part 130 is in the form of a crossbar as discussed in more detail below. In one embodiment, the first piece has a first socket, and the second piece has a second socket where the third part or crossbar member is at least partially received in the first socket and the second socket. In an embodiment, the crossbar member has a first bar that is mounted above a second bar and in an embodiment perpendicular to the first bar.

The upper plate 110 has a first surface 112 from which a keel 114 extends with teeth 115. The teeth in this embodiment point forward or anteriorly when the embodiment is meant to be put into a slot in a vertebral body from the anterior of the spine. The teeth in an alternative embodiment would point rearward or posteriorly when the embodiment is meant to be put into a slot in a vertebral body from the posterior of the spine. The first surface 112, or upper surface, abuts the vertebral body when the implant 100 is implanted. The first keel 114 extends into the vertebral body to anchor the implant into position. The second surface 116, or lower surface, engages the spacer 130 of the implant and faces the second plate 120. The second surface 116 can form a planar surface that is parallel to the first surface 112, or can form a planar surface that is not parallel to the first surface 112.

When the implant is implanted between spinous processes the planar surfaces corresponding to the first surface 112 and the second surface 116 of the first plate 110 lie within, or substantially within, the axial plane of the body, while the first keel 114 (which is at or near a 90° angle from the surfaces 112, 116) is aligned within the sagittal plane of the body.

The lower plate 120 has a first surface 122 from which a keel 124 extends with teeth 125. The first surface 122, or lower surface, abuts the vertebral body when the implant 100 is implanted. The second keel 124 extends into the vertebral body to anchor the implant into position. The second surface 126, or upper surface, engages the spacer 130 of the implant and faces the first plate 110. The second surface 126 can form a planar surface that is parallel to the first surface 122, or can form a planar surface that is not parallel to the first surface. The first surface 112 of the first plate 110 can be parallel to the first surface 122 of the second plate 120 when the implant 100 is assembled and is in a neutral position (i.e., the position where the first plate 110 has not rotated relative to the second plate 120). Alternatively, the first surface 112 of the first plate 110 can be non-parallel to the planar surface of the first surface 122 of the second plate 120 when the implant 100 is assembled and in a neutral position.

As with the first plate, when the implant is implanted between vertebral bodies the planar surfaces corresponding to the first surface 122 and the second surface 126 of the second plate 120 lie within, or substantially within, the axial plane of the body while the second keel 124 (which is at or near a 90° angle from the surfaces 122, 126) is aligned within the sagittal plane of the body.

Figure 1B:
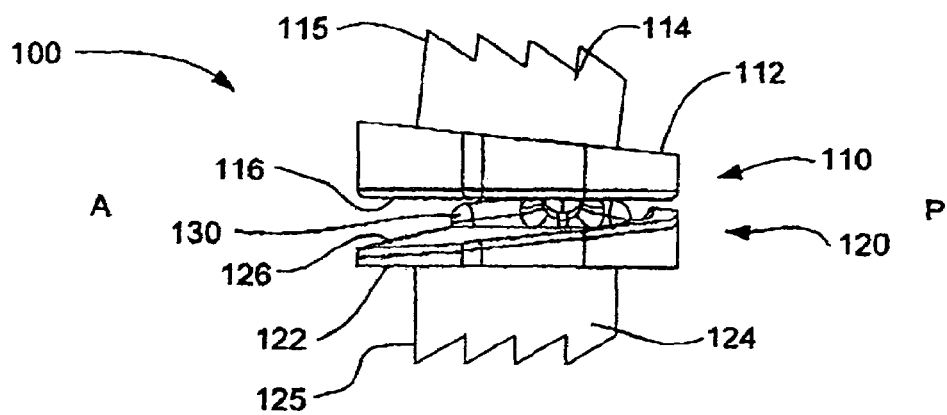
FIG. 1B is a side view of an embodiment of an implant of the invention.
Figure 1C:
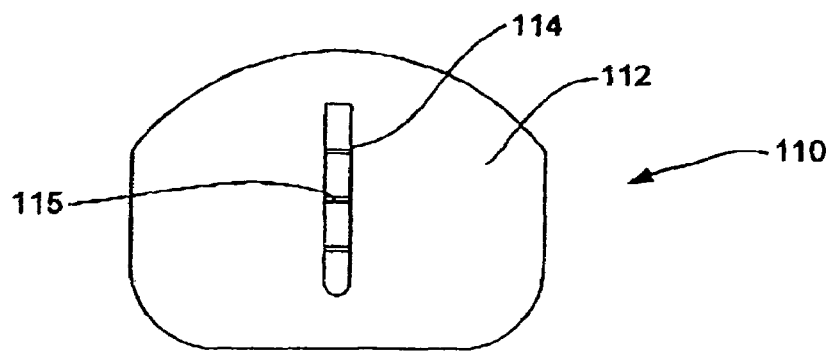
FIG. 1C is a top view of an embodiment of the implant of the invention.

FIG. 1B shows a side view of an embodiment of the implant 100 of the invention shown in FIG. 1A. Again, the implant 100 has a first plate 110 that is configured to mate with a first vertebra and a second plate 120 that is configured to mate with a second vertebra. The spacer 130 separates the first plate 110 from the second plate 120. FIG. 1C shows a top view of the upper plate 110 with the upper surface 112 and the upper keel 114. As evidenced from the upper view, the perimeter shape of the upper plate 110 can be configured to correspond to the perimeter shape of a vertebral disk. This is particularly advantageous where a single implant is placed between two vertebral bodies from an anterior approach. As will be appreciated by those of skill in the art, the perimeter shape of the upper plate 110 and the lower plate 120 can be the same.

Figure 1D:
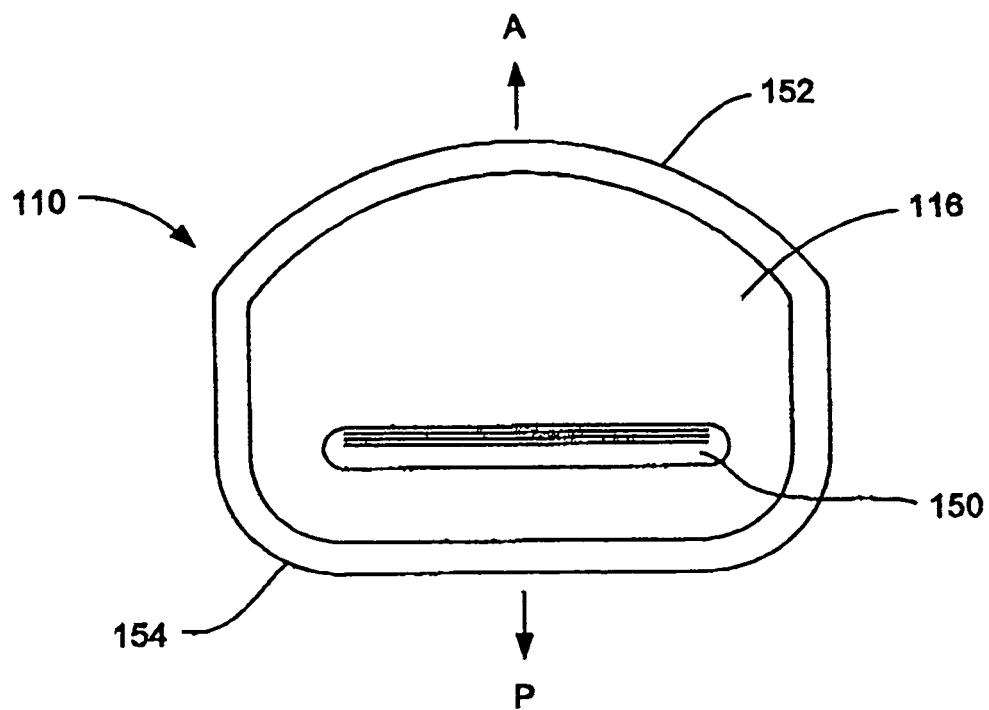
FIG. 1D is a top view of an embodiment of the first surface of the top plate of the implant of the invention.
Figure 1E:
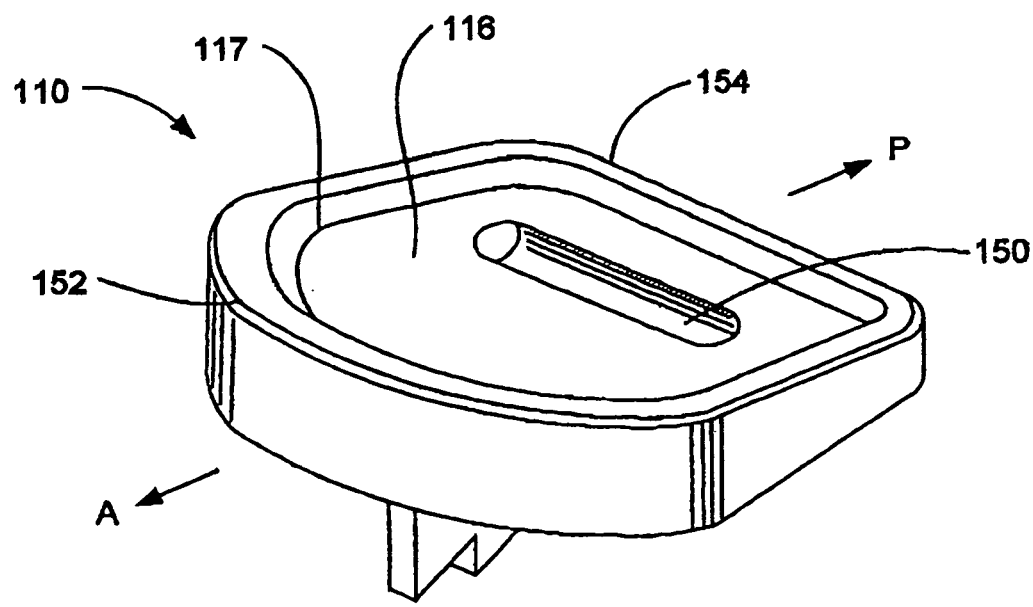
FIG. 1E is a perspective view of an embodiment of the upper plate of the implant of the invention.

FIG. 1D and FIG. 1E show an embodiment of the first or upper plate 110 of the implant 100 of the invention. The upper plate 110 has a second surface 116 having a channel 150 therein. As will be discussed below, the spacer includes a beam which can be placed into the channel 150 in order to allow the first and second plates of the assembled implant to pivot or rotate relative to each other. The curved side 152 of the first plate 110 is oriented to be anterior A after the device is implanted. The flat side 154 of the first plate 110 is oriented to be posterior P after the device is implanted. As shown in FIG. 1E, the second surface 116 can be formed so that it is received with a ridge 117 surrounding the second surface 116.

Figure 1F:
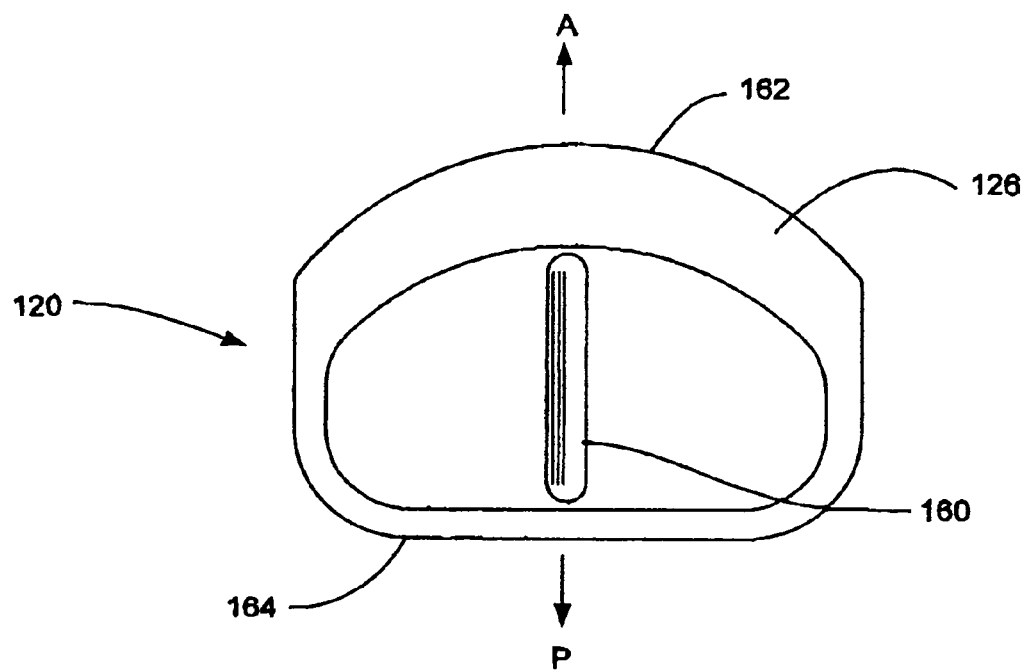
FIG. 1F is a plan view of the first surface of the lower plate of an embodiment of the implant of the invention.
Figure 1G:
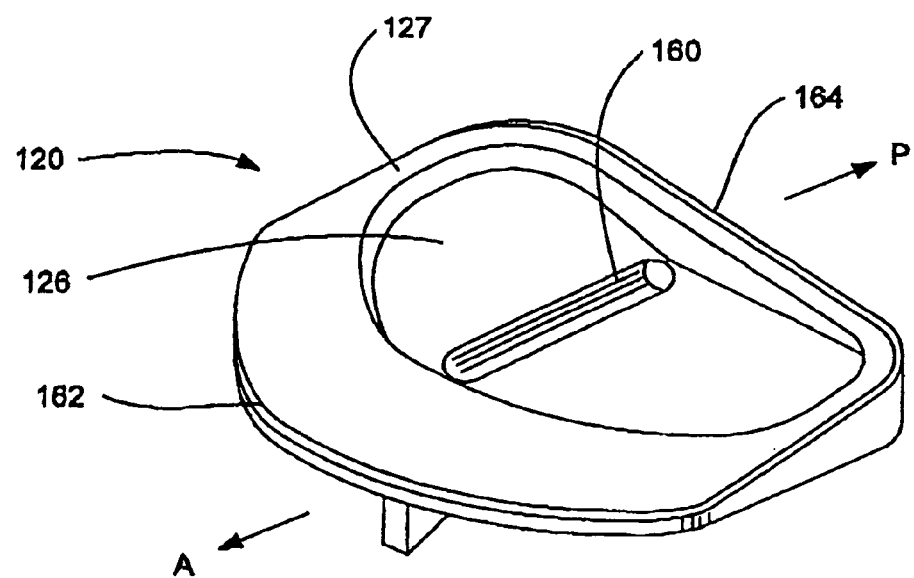
FIG. 1G is a perspective view of the lower plate of an embodiment of the implant of the invention.

FIG. 1F and FIG. 1G show the second or lower plate 120 of the implant 100 of the invention. The lower plate 120 has a second surface 126 having a channel 160 therein. As will be discussed below, the spacer includes a beam which can be placed into the channel 160 in order to allow the first and second plates of the assembled implant to pivot or rotate relative to each other. The curved side 162 of the second plate 120 is oriented to be anterior A after the device is implanted. The flat side 164 of the second plate 120 is oriented to be posterior P after the device is implanted. As shown in FIG. 1G, the second surface 126 can be formed so that it is recessed with a ridge 127 surrounding the second surface 126.

Figure 1H:
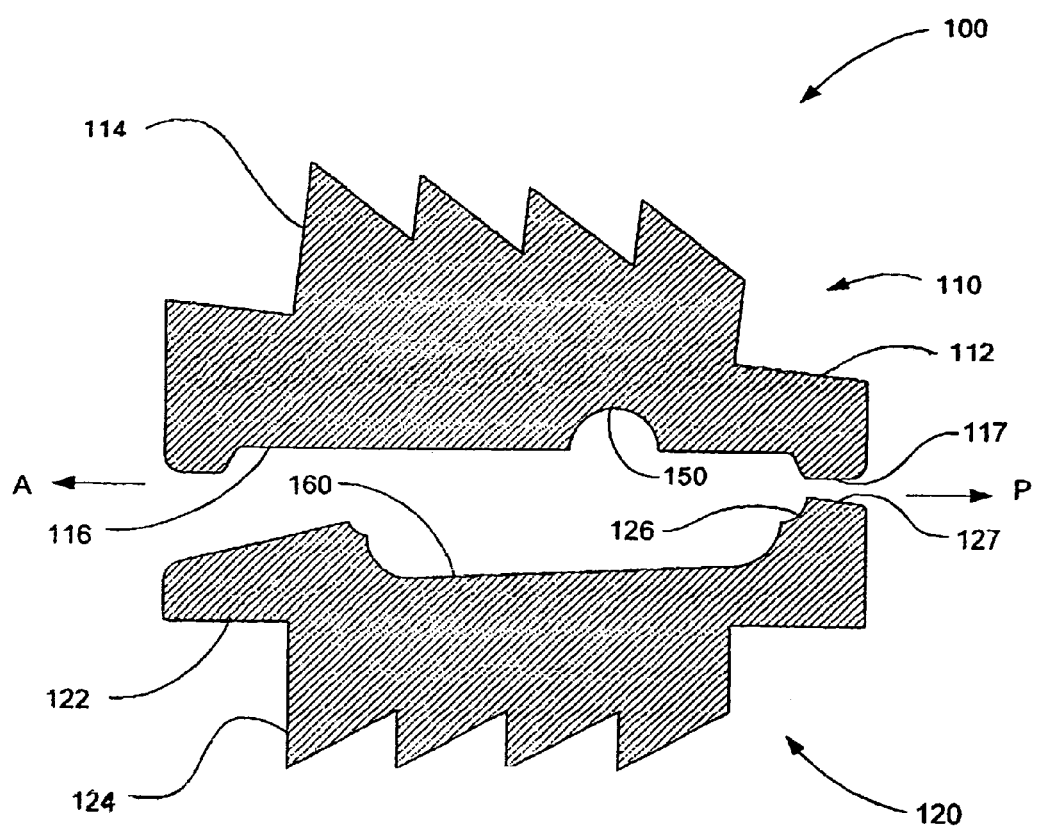
FIG. 1H is a cross-sectional view of the upper and lower plates of an embodiment of the implant of the invention taken at H-H in FIG. 1A.

FIG. 1H is a cross-section of the upper plate 110 and the lower plate 120 taken along the lines H-H of FIG. 1A. As shown in FIG. 1H, the second surface 116 of the first plate 110 faces the second surface 126 of the second plate 120.

In FIG. 2, the crossbar or spacer 130 is shown. FIG. 2A is an upper view of an embodiment of a crossbar or spacer 130 of the implant of the invention. The crossbar 130 has a first beam 210 and a second beam 220. Each beam 210, 220, has a first end 212, 222, and a second end 214, 224, and a midpoint 216, 226, respectively. FIG. 2B shows a side view of a crossbar 130 of the implant 100 of the invention. As is apparent from the side view, the first beam 210 can be configured to sit above the second beam 220. FIG. 2c shows the crossbar 130 of the implant of the invention from a bottom view with the first beam 210 configured to sit above the second beam 220.

The first beam 210 can be configured to be positioned transversely along the length of the second beam 220 at a point preferably corresponding about the midpoint 226 of the second beam 220. The second beam 220 can be configured to be positioned along the length of the first beam 210 at a point preferably corresponding about the midpoint 216 of the first beam 210. Where both beams are positioned at the respective midpoints 216, 226 the crossbar forms a "+".

In the alternative embodiment, the first beam 210 can also be configured to be positioned transversely along the length of the second beam 220 at a point corresponding to a location between the midpoint 226 and an end (222, 224). The second beam 220 can be configured to be positioned transversely along the length of the first beam 210 at a point corresponding to about the midpoint 216 of the first beam 210. Where one beam 210, 220 is positioned along the length between the midpoint and an end of the other beam, the crossbar forms "T".

In constructing the crossbar 130, the first beam 210 can be formed integrally with the second beam 220 such that is unitary in construction. Alternatively, the first beam 210 can be adhered to the second beam 220 using a suitable method, such as spot welding.

Figure 2A:
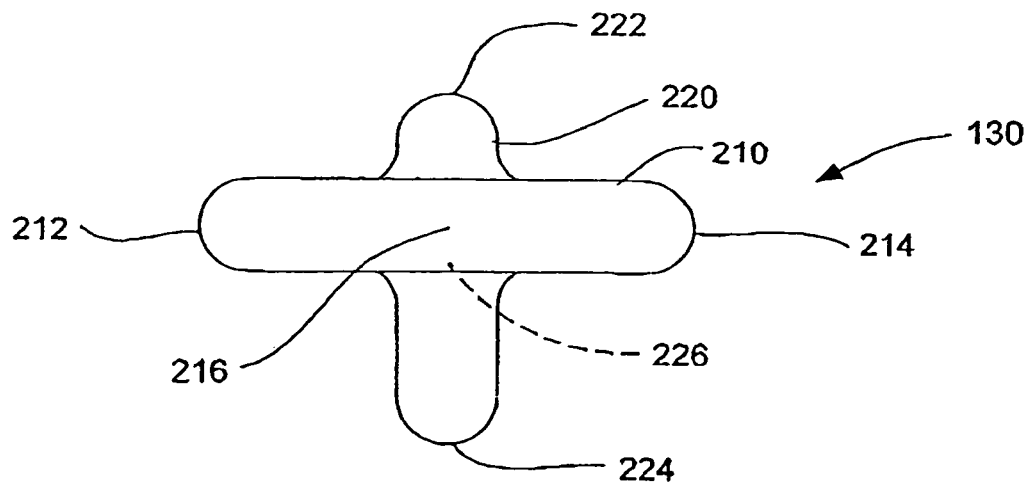
FIG. 2A is an upper view of a crossbar of an embodiment of the implant of the invention.
Figure 2B:
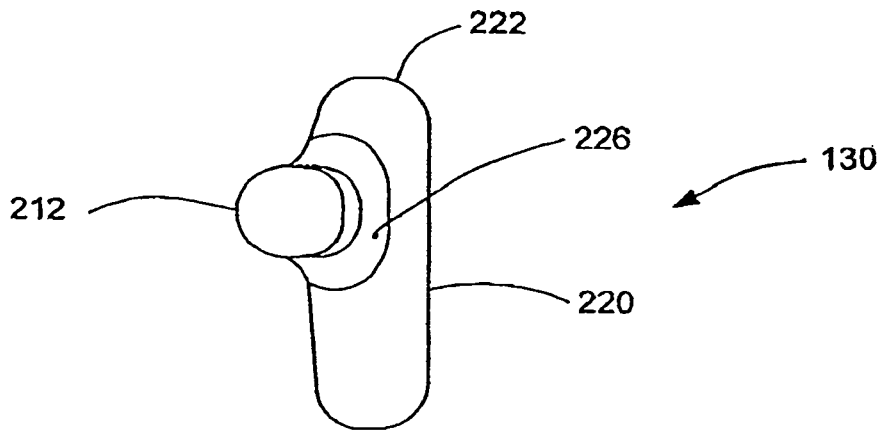
FIG. 2B is a side view of a crossbar of an embodiment of the implant of the invention.
Figure 2C:
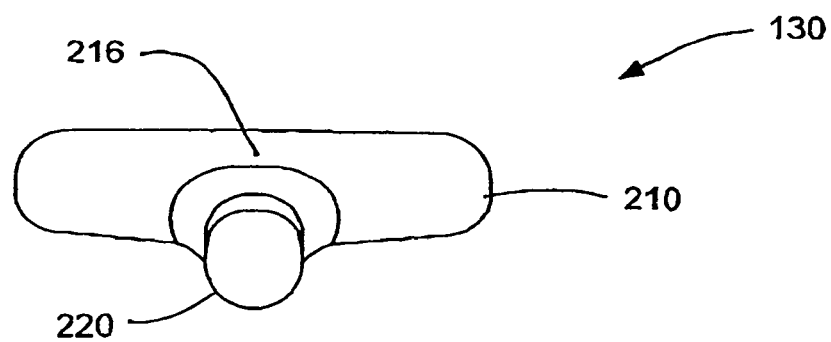
FIG. 2c is a lower view of a crossbar of an embodiment of the implant of the invention.
Figure 2D:
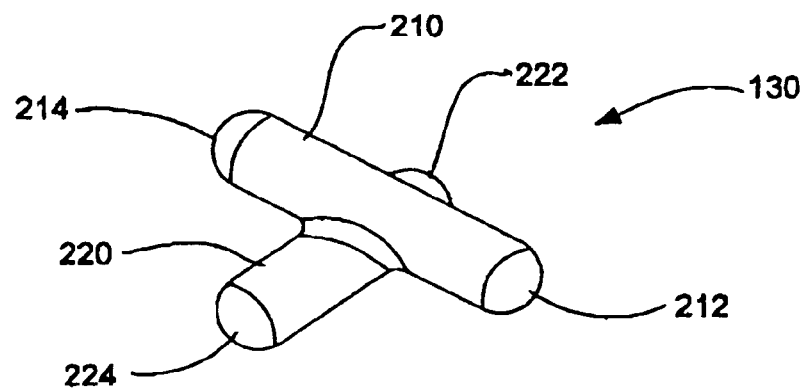
FIG. 2D is a perspective view of a crossbar of an embodiment of the implant of the invention.

FIG. 2D shows a perspective view of a crossbar or spacer 130 of the implant of the invention. As shown in FIG. 2D, the first beam 210 and the second beam 220 are configured so that the second beam 220 is positioned along the length of the first beam 210 at a point between the midpoint 226 of the second beam 220 and an end 222 of the second beam 220.

Figure 3:
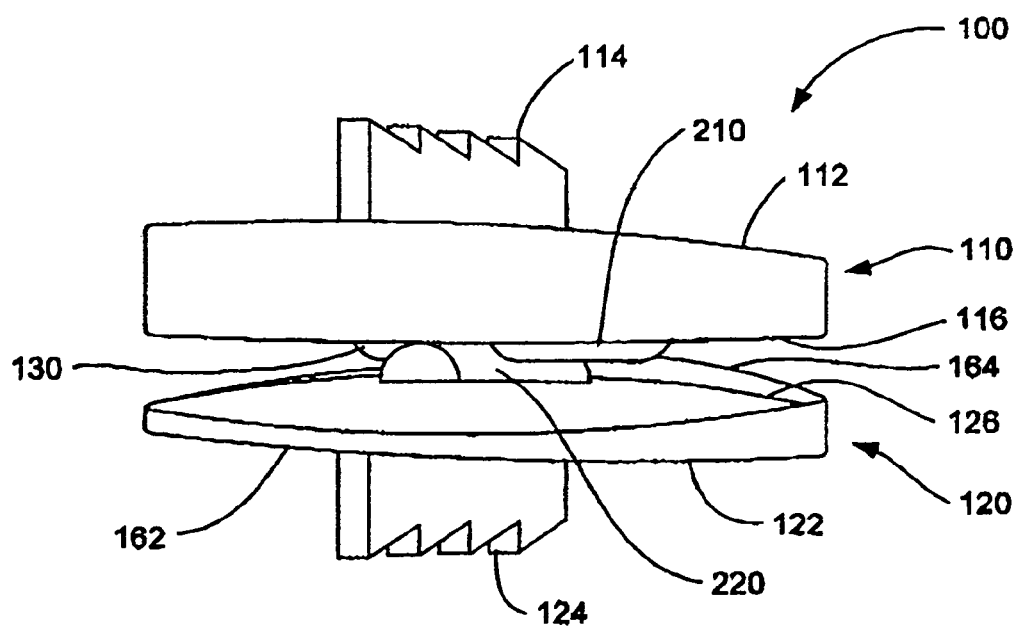
FIG. 3 is a perspective view of an assembled implant of an embodiment the invention.

Viewing FIGS. 1A, 1B and 3, an assembled embodiment of the implant 100 of the invention is depicted. The implant 100 has a first plate 110 that is configured to mate with a first vertebra and a second plate 120 that is configured to mate with a second vertebra. A crossbar 130 that sits between the first plate 110 and the second plate 120 is also provided. As is evident from the figures, the upper beam 210 is placed in the channel 150 of the upper plate 110 such that the upper beam is about perpendicular to the keels 114 and 124. As can be seen from FIG. 1B, the upper beam is positioned toward the posterior of the implant 100. In alternative embodiments the upper beam can be positioned midway between the posterior and the anterior of the implant 100. The lower beam 220 is placed in the channel 160 of the lower plate 120 such that the lower beam is about parallel to the keels 114 and 124. The crossbar 130 acts as a spacer between the first plate 110 and the second plate 120 and facilitates pivotal or rotational movement of the first plate 110 and the second plate 120, relative to each other. With the implant 100 placed between vertebral bodies of a patient, the keels 114 and 124 are directed along a posterior to anterior line or in the sagittal plane of the patient. Accordingly as the patient bends forward or backward the upper plate 110 can pivot or rotate about the beam 210. When the patient bends laterally or side to side, the lower beam 220 can pivot or rotate in the lower channel 160, allowing the upper beam 210 to pivot or rotate about the lower beam 220 and also allowing the upper plate 110 to pivot or rotate about the lower beam 220, and, thus, relative to the lower plate 120. In an alternative embodiment, there is a loose fit between the spacer 130 and the first and second plates, and, in particular, there is a loose fit between the upper beam 210 and the upper channel 150 and also between the lower beam 220 and the lower channel 160. This loose fit allows for a twisting motion about an axis that is perpendicular to the plates as, for example, perpendicular to the surface 112 of the upper plate. Thus, this loose fit allows for twisting about the length of the spine.

As illustrated in FIGS. 1B, 1G and 3, the ridge 127 adjacent to the second surface 126 of the lower plate is not parallel to the first surface 122 of the lower plate nor to the upper plate.

The orientation of the plates 110, 120 in FIGS. 1A, 1B and 3, show the implant 100 assembled in a neutral position (i.e., the position where the first plate 110 has not rotated relative to the second plate 120). The distance between the first plate 110 and the second plate 120 enable the implant to achieve movement in forward, backward, lateral and rotational directions.

Figure 4:
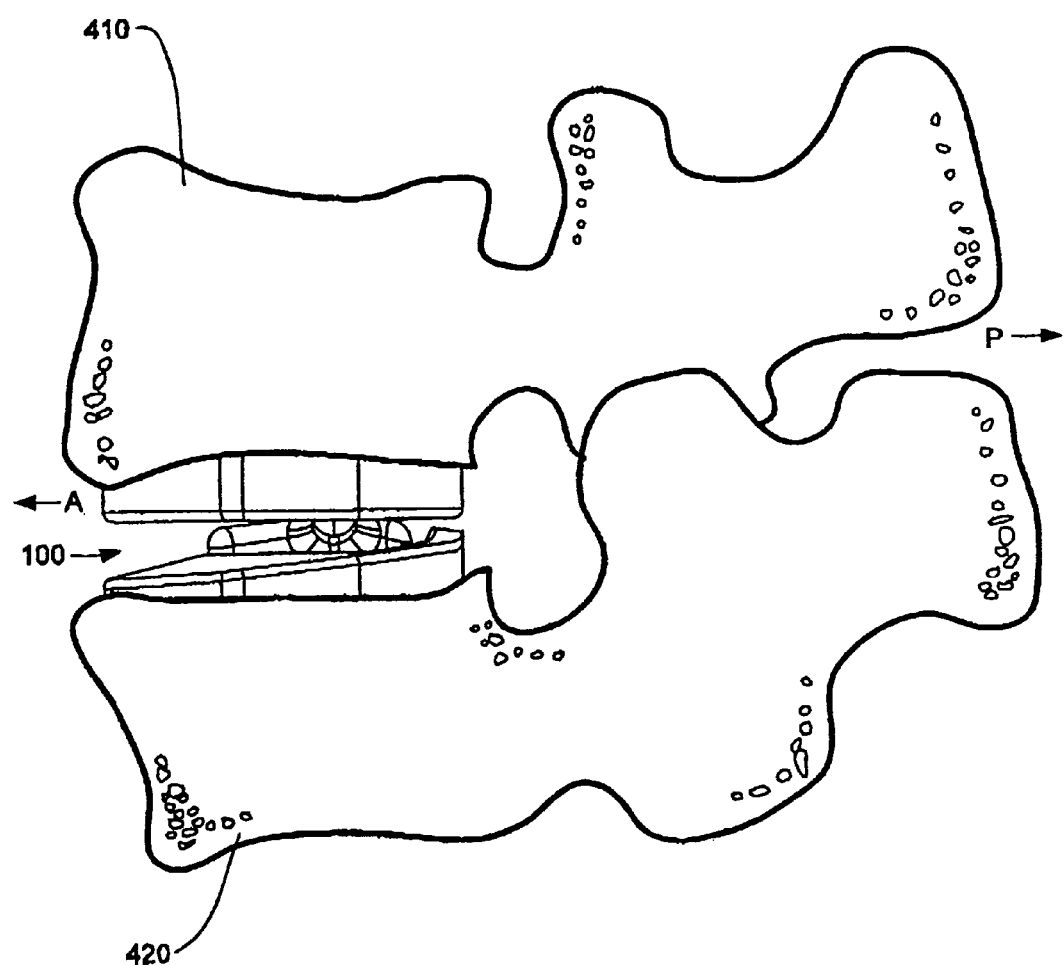
FIG. 4 is a side view of the implant implanted between the vertebral bodies.
Figure 5:
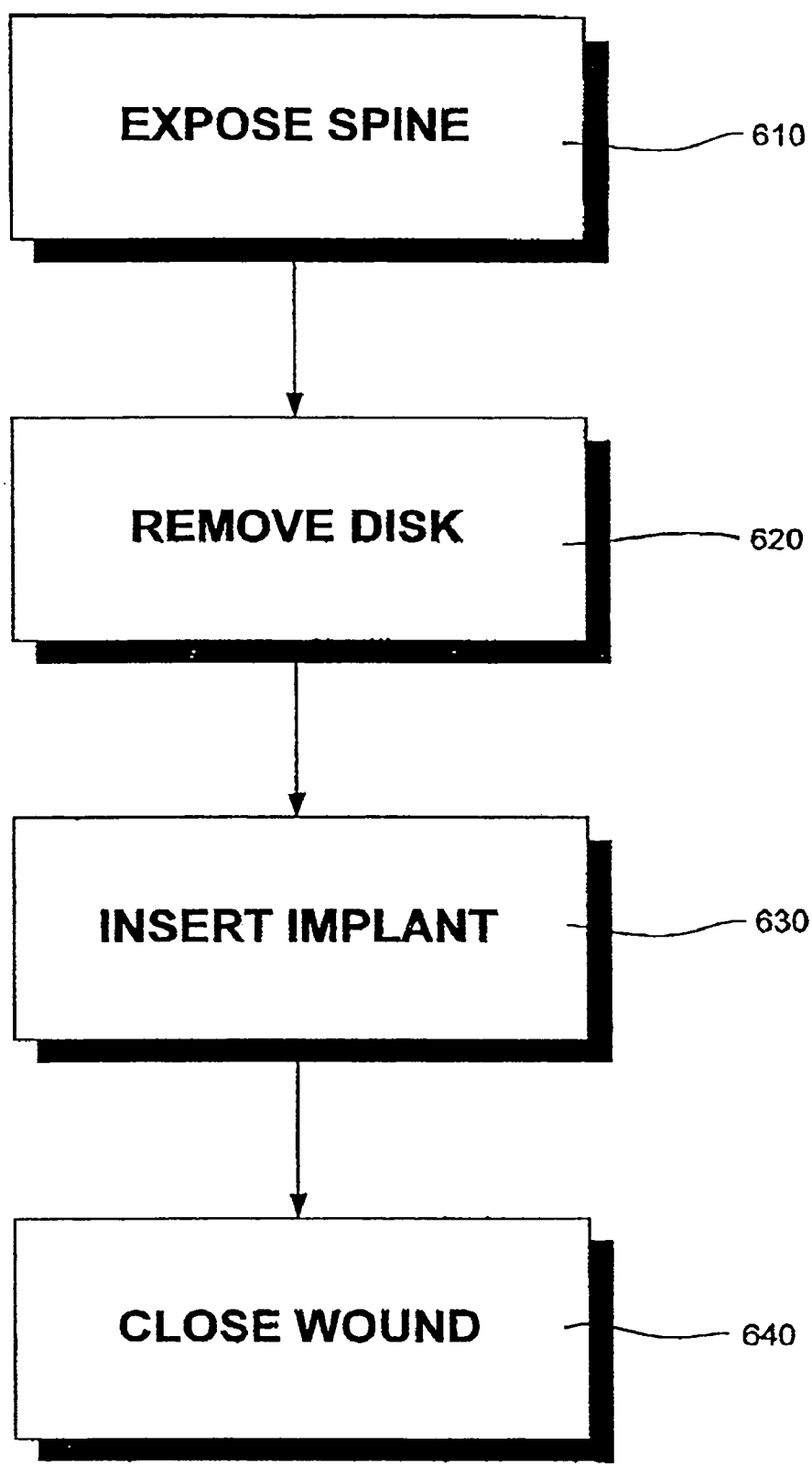
FIG. 5 is a block diagram showing the method steps for implanting the implant of the invention.

FIG. 4 shows a side view of an implant 100 of the invention implanted between two vertebrae 410, 420. Given the difference between the first plate 110 and the second plate 120 at its anterior end A and its posterior end P, i.e., the distance between the plates is greater at the anterior A end than the posterior P end, forward (bending) movement is facilitated to a greater degree than backward (bending) movement. Thus, for this embodiment, an example of a forward bending movement of up to 10° can be achieved while a backward bending movement of 5° will be achieved. By sloping the lower plate and/or the upper plate toward the posterior portion, the amount of backward bending can be increased.

In a preferred embodiment, the implant can be made of titanium or a stainless steel that is approved for implantation into a patient. Other materials that have appropriate structural strength and that are suitable for implantation into a patient can also be used.

FIG. 6 is a block diagram showing the basic steps of the method of inserting the implant 100 of this invention. First the spine is exposed 610, then the intervertebral disk is removed 620 and the implant is inserted 630. Finally, the wound is closed 640. This procedure can be followed for either an anterior approach or posterior-lateral approach. Additional steps, such as cutting channels into the vertebral bodies to accept the keels of the plates and assembling the implant by inserting the crossbar member between the upper and lower plates prior to installation can also be performed without departing from the scope of the invention.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and its equivalence.

An implant with a first piece having a first socket, a second piece having a second socket and a crossbar member that is at least partially received in the first socket and the second socket, wherein the first piece has a first surface and a second surface wherein the first socket is located on the first surface and a keel extends from the second surface, wherein the second piece has a first surface and a second surface wherein the second socket is located on the first surface and a keel extends from the second surface, wherein the keel is oriented in a first plane and the first socket is oriented in a second plane, and further wherein the first plane and the second plane are perpendicular to each other.

An implant with a first piece having a first socket, a second piece having a second socket and a crossbar member that is at least partially received in the first socket and the second socket, wherein the first piece has a first surface and a second surface wherein the first socket is located on the first surface and a keel extends from the second surface, wherein the second piece has a first surface and a second surface wherein the second socket is located on the first surface and a keel extends from the second surface, wherein the keel is oriented in a first plane and the first socket is oriented in a second plane, and further wherein the first plane and the second plane are parallel to each other.

What is claimed:

1. An implant adapted to be placed between two vertebral bodies comprising:
    an upper implant further comprising, a first surface that is adapted to contact a bottom surface of an upper vertebral body, and a second surface having a first concave socket;
    a lower implant further comprising, a first surface that is adapted to contact an upper surface of a lower vertebral body, and a second surface having a second concave socket; and
    a crossbar member with a first beam that is received in the first concave socket of the upper implant and a second beam that is received in the second concave socket of the lower implant, wherein after an implant is inserted and the patient has healed at least one of the upper and lower implant remains capable of pivoting about the crossbar; wherein at least one of the upper implant and the lower implant are moveable about the crossbar member to allow a twisting motion of said piece.

2. The implant of claim 1, wherein the first beam and the second beam are perpendicular.

3. The implant of claim 1, wherein the crossbar member can pivot on itself.

4. The implant of claim 1, wherein one of the first socket and second socket is sloped to allow rocking motion.

5. The implant of claim 1, wherein the first beam of the crossbar crosses the second beam of the crossbar at a midpoint along the second beam.

6. The implant of claim 1, wherein the first beam of the crossbar and the second beam of the crossbar are formed integrally.

7. The implant of claim 1, wherein the second socket in the second piece is oriented to lie in a plane perpendicular to a sagittal plane of a patient.

8. An implant sized to be inserted between adjacent vertebrae comprising:
    a first piece having a first socket;
    a second piece having a second socket; and
    a crossbar member wherein the crossbar includes a first beam and a second beam that are at least partially received in the first socket and the second socket respectively, wherein after an implant is inserted and the patient has healed at least the first piece remains capable of pivoting about the crossbar member to accommodate at least one of flexion, extension and lateral bending; wherein at least one of the first piece and the second piece are moveable about the crossbar member to allow a twisting motion of said piece.

9. The implant of claim 8, wherein the first beam is received in the first socket and the second beam is received in the second socket.

10. The implant of claim 8, wherein the first beam and the second beam of the crossbar form a cross.

11. The implant of claim 8, wherein the first beam of the crossbar abuts the second beam of the crossbar.

12. The implant of claim 8, wherein the first beam of the crossbar crosses the second beam of the crossbar at a midpoint along the second beam.

13. The implant of claim 8, wherein the first beam of the crossbar and the second beam of the crossbar are formed integrally.

14. The implant of claim 8, wherein the first beam of the crossbar and the second beam of the crossbar are adhered to each other.

15. The implant of claim 8, wherein the first beam of the crossbar crosses the second beam of the crossbar at a midpoint of the second beam and at an end point of the second beam.

16. The implant of claim 8, wherein the first beam of the crossbar is positioned at least partially above the second beam of the crossbar.

17. The implant of claim 8, wherein the first beam of the crossbar and the second beam of the crossbar are adhered to each other.

18. The implant of claim 8, wherein the crossbar member can pivot on itself.

19. The implant of claim 8, wherein the first beam of the crossbar is positioned partially or completely above the second beam of the crossbar.

* * * * *